US008973575B2

(12) United States Patent
Tigerstedt

(10) Patent No.: US 8,973,575 B2
(45) Date of Patent: Mar. 10, 2015

(54) ANAESTHESIA MACHINE ARRANGEMENT AND A METHOD IN CONNECTION WITH AN ANAESTHESIA MACHINE ARRANGEMENT

(75) Inventor: Erik Wilhelm Severin Tigerstedt, Espoo (FI)

(73) Assignee: Carefusion Corporation, San Diego, CA (US)

(*) Notice: Subject to any disclaimer, the term of this patent is extended or adjusted under 35 U.S.C. 154(b) by 1782 days.

(21) Appl. No.: 12/052,328

(22) Filed: Mar. 20, 2008

(65) Prior Publication Data

US 2008/0236583 A1 Oct. 2, 2008

(30) Foreign Application Priority Data

Mar. 29, 2007 (EP) .................................... 07105168

(51) Int. Cl.
*A61M 16/01* (2006.01)
*A61M 16/10* (2006.01)
*A61M 16/00* (2006.01)
*A61M 16/22* (2006.01)

(52) U.S. Cl.
CPC ......... *A61M 16/104* (2013.01); *A61M 16/0051* (2013.01); *A61M 16/01* (2013.01); *A61M 16/22* (2013.01); *A61M 2016/1025* (2013.01); *A61M 2016/1035* (2013.01); *A61M 2202/0208* (2013.01); *A61M 2202/0283* (2013.01); *A61M 2205/15* (2013.01); *A61M 2230/435* (2013.01); *A61M 2230/437* (2013.01)
USPC ............. 128/203.14; 128/203.25; 128/204.22

(58) Field of Classification Search
CPC ............ A61M 16/00; A61M 16/0003; A61M 16/0051; A61M 16/01; A61M 16/0104; A61M 16/22; A61M 2016/1035
USPC .......................... 128/202.22, 203.12–203.14, 128/203.25–203.27, 204.18, 204.21, 128/204.22, 204.26; 600/532, 529; 73/23.3
See application file for complete search history.

(56) References Cited

U.S. PATENT DOCUMENTS

| 5,094,235 | A  | * | 3/1992  | Westenskow et al. ... 128/204.22 |
| 5,558,083 | A  | * | 9/1996  | Bathe et al. .............. 128/203.12 |
| 5,584,291 | A  |   | 12/1996 | Vapola et al. |
| 5,957,129 | A  | * | 9/1999  | Tham et al. ............... 128/204.28 |
| 6,131,571 | A  | * | 10/2000 | Lampotang et al. ...... 128/204.21 |
| 6,892,726 | B1 | * | 5/2005  | Heinonen et al. ........ 128/202.22 |
| 7,290,544 | B1 | * | 11/2007 | Serala et al. ............. 128/202.22 |
| 2005/0103338 | A1 |  | 5/2005  | Bunke et al. |

FOREIGN PATENT DOCUMENTS

EP 1140264 B1 11/2005
WO WO 00/33904 6/2000

* cited by examiner

*Primary Examiner* — Valerie L Skorupa
(74) *Attorney, Agent, or Firm* — McDermott Will & Emery LLP

(57) ABSTRACT

Anaesthesia machine arrangement and a method in connection with an anaesthesia machine arrangement comprising a gas dispenser of an anaesthesia machine connected to a patient circuit that comprises a monitor device, a control device and an interface unit. The gas dispenser is configured to deliver a desired concentration of fresh gas to the patient circuit, the desired concentration being set by using the interface unit. The monitor device is configured by using a sample line to monitor gas concentration in the patient circuit and the control device is configured to control the gas dispenser from the basis of the data received from the monitor device to keep the desired fresh gas concentration.

16 Claims, 1 Drawing Sheet

ANAESTHESIA MACHINE ARRANGEMENT AND A METHOD IN CONNECTION WITH AN ANAESTHESIA MACHINE ARRANGEMENT

CROSS-REFERENCE TO RELATED APPLICATIONS

This application claims, under 35 U.S.C. 119 (a)-(d), right of priority to the earlier filing date of prior-filed, co-pending European Community Patent Application No: 07105168.4, filed Mar. 29, 2007. The basis for this claim to the right of priority is the European Community's membership in the World Trade Organization ("WTO").

BACKGROUND OF THE INVENTION

Embodiments of the invention relate to an anaesthesia machine arrangement comprising a gas dispenser of an anaesthesia machine connected to a patient circuit comprising a CO2 absorber, a monitor device, a control device and an interface unit, whereby the gas dispenser is configured to deliver a desired concentration of fresh gas to the patient circuit, the desired concentration being set by using the interface unit, the monitor device is configured by using a sample line to monitor gas concentration in the patient circuit and the control device is configured to control the gas dispenser from the basis of the data received from the monitor device to keep the desired fresh gas concentration. The invention relates also to a method in connection with an anaesthesia machine arrangement.

A basic requirement set for devices used in patient care is that they are safe and operationally reliable in the normal use of the device, in fault situations unintentionally caused by a user or in any one-fault situation of the device.

Anaesthesia machines and ventilators used in intensive care and anaesthesia can be mentioned as examples of the devices described above. A patient is normally connected to a device used in patient care, e.g. an anaesthesia machine and ventilator, by means of a patient circuit. From the patient circuit there is a measuring connection to a monitor, which monitors the condition of the patient. Using measuring information on the condition of the patient a healthcare person supervises the condition of a patient and adjusts set values of the device used in patient care so that the measuring information corresponds to the desired value of the moment.

Due to the indirectness and in some circumstances long time constant the exact adjustment of measuring values is slow and difficult, which leads to variation in patient values, and this in turn may have harmful effects on the end result in nursing.

To improve the situation, a variety of solutions have been suggested for automatizing the systems used in the situations described above. In other words it has been suggested that a system, i.e. a machine and not a person, takes automatically care of adjusting steps needed to obtain a result desired. When discussing about automatic systems here we mean that automatic delivery of breathing gases to the patient refers to a system where the desired concentration in breathing gases is set and the machine used keeps it correct by automatically adjusting the fresh gas (FG) flow concentration. When using automatic systems it is however essential that for example in an automatic system delivering a mixture of anaesthetic agent, N2O and oxygen to the patient to be treated, there must be some way to assure that a device failure does not cause the system to deliver wrong concentration to the patient.

In order to achieve a safely level high enough double monitoring is used in the prior art. In double monitoring two or even more monitors are used so that a fault in one monitor can be brought to the user's attention if the monitors show different readings.

The disadvantages of this known technique is the high cost of double monitoring, i.e. double or in some cases even more than double monitoring hardware leads to high costs.

As another example of the prior art a system using one monitor and a sample system can be mentioned. In this system one monitor is used and samples are taken from either the fresh gas used or from some other known gas. The fresh gas concentration is known. If the fresh gas sample readings are wrong one knows that either the anaesthesia machine or monitor does not work correctly. This known system is described in EP Patent 1 140 264 B1.

Prior art systems, i.e. both the traditional person-based systems and the automatic systems have a common disadvantage, which may cause severe risks during anaesthesia. This disadvantage is caused by eventual sampling line leaks. Said leaks can cause the gas sample to be diluted by ambient air. This again can cause the anaesthesia machine used or the person taking care of the steps to be carried out to over deliver, i.e. to overdose the anaesthetic agent to be delivered to the patient treated.

Currently it is difficult to detect a leak. The absence of CO2 or N2O or presence of N2 can in some cases be used for detection but if the leak is small, these known methods are not reliable.

SUMMARY OF THE INVENTION

Embodiments of the invention provide an arrangement by which the prior art disadvantages can be eliminated. This is achieved by the arrangement according to an embodiment of the invention. The arrangement of the invention is characterized in that the monitor device is configured to monitor and indicate change in measured sampling gas concentration that correlates with the change in the patient circuit pressure for leak detection. The method of the invention is characterized in that change in the measured sampling gas concentration that correlates with the change in the patient circuit pressure for leak detection is monitored and indicated.

An advantage of embodiments of the invention is that they create a means of detecting small leaks in the patient circuit continuously in anaesthesia environment. This has not been possible before the invention.

BRIEF DESCRIPTION OF THE DRAWINGS

In the following brief description of the drawings, embodiments of the invention will be described in greater detail by means of the attached drawing in which.

DETAILED DESCRIPTION

Figure 1:
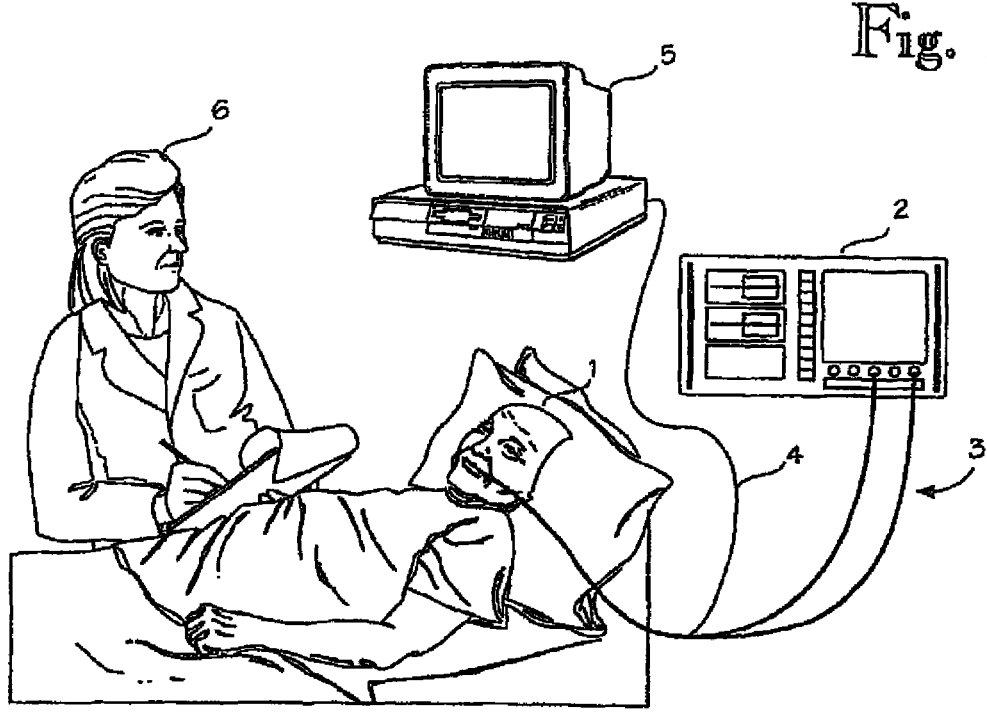
FIG. 1 shows a schematic view of an operational environment of equipment used in patient care.

FIG. 1 shows a schematic view of an operational environment of equipment used in patient care. A patient 1 is connected to a device used in patient care, which, in the example of FIG. 1, is a combination of a gas mixer and ventilator 2. The patient is connected by means of a patient circuit 3. From the patient circuit 3 there is a measuring connection 4 to a monitor 5, which monitors the condition of the patient. A healthcare person 6 supervises the condition of the patient on the basis of the measuring information on the condition of the patient provided by the monitor 5 and, when necessary, adjusts set values of the device used in patient care such that the measuring information corresponds to the desired value of the moment, as described above.

Figure 2:
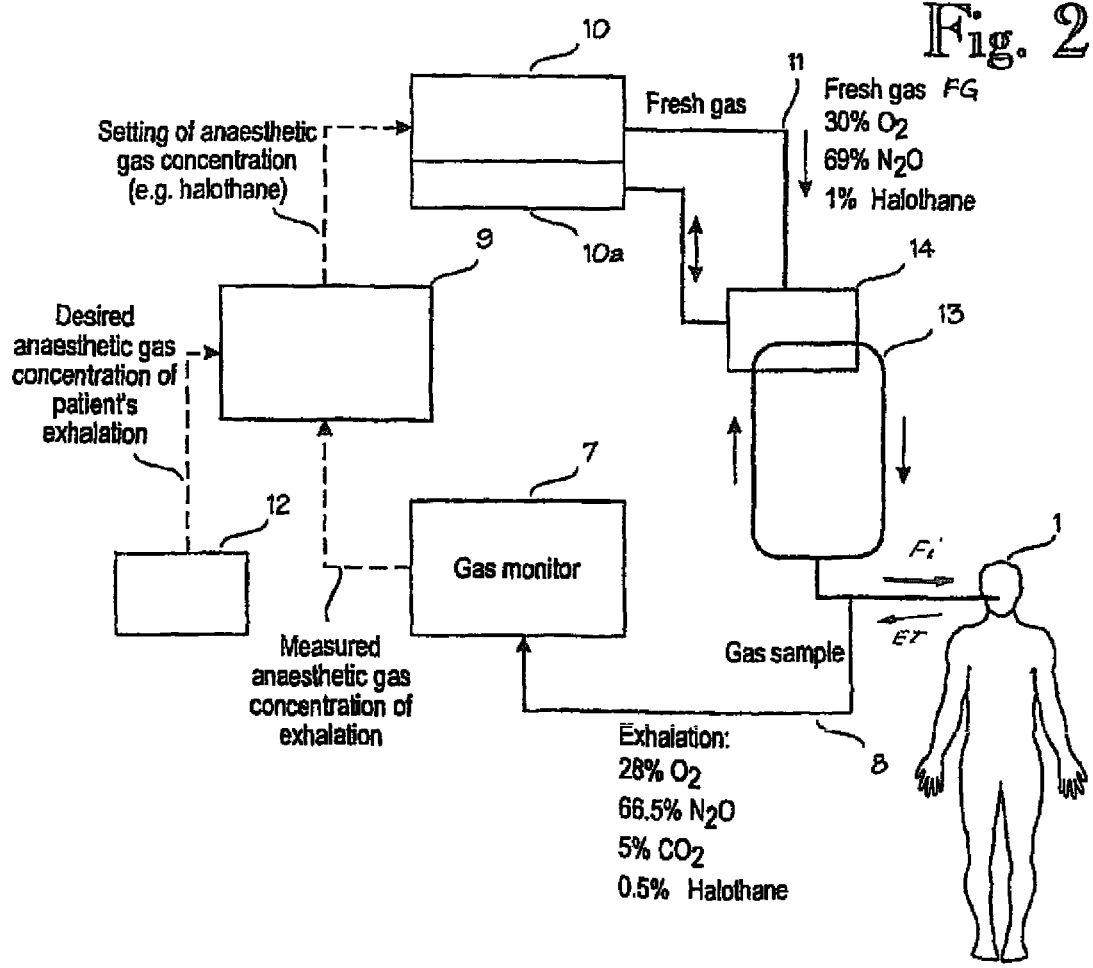
FIG. 2 shows a diagram of an example of an automatic control arrangement of a gas dispenser in an anaesthesia machine.

FIG. 2 shows a control system, in which a gas dispenser of an anaesthesia machine is automatically controlled on the basis of a signal given by breathing gas measurement of the monitor. If, as a result of a fault situation, a gas monitor 7 measures a lower anaesthetic gas concentration from a sample flowing through a sample line 8 than it in fact is or does not measure it at all, a controller 9 sets a gas dispenser 10, to produce a higher anaesthetic gas concentration than it actually should be according to the value set by a user with an interface unit 12. This leads to an overdose of the anaesthetic and thus to a dangerous situation. Gas concentrations shown in FIG. 2 are only example values. In FIG. 2 a patient circuit is indicated with the reference number 13, a CO2 absorber with the reference number 14 and a ventilator with the reference number 10*a*. As in the example of FIG. 1 a patient is marked with the reference number 1.

In principle, the system of FIG. 2 operates in the following way. While a patient is under treatment, the gas dispenser 10 feeds a desired gas mixture to the patient 1 and the gas monitor 7 measures the anaesthetic gas concentration and informs the controller 9 of it. The controller 9 adjusts the setting of the anaesthetic gas concentration in order to achieve the desired end result. The user has naturally set a desired gas concentration of the patient's exhalation to the controller 9 by using the interface unit 12. The operation of the controller 9 can be based for example on fuzzy logic.

Both the traditional human-based system shown in FIG. 1 and the automatic system shown in FIG. 2 have the disadvantage described before i.e. risk situations caused by sampling line leaks. As told before especially detecting small leaks in the patient circuit has not been possible in the prior art.

The present invention creates a solution by which the disadvantage described above can be eliminated in very efficient and simple manner. The present invention can also be used as an indicator that in fuzzy logic utilizing leak calculation tells that the probability for a leak has risen.

Because of the higher than ambient pressure in the patient circuit the only small leak that has any relevance is a leak that happens at the monitor end, i.e. near monitor 5 in FIG. 1 or near monitor 7 in FIG. 2. Small leaks at the patient end will not cause the sampling gas to be diluted. It will only cause the patient gases to leak out. Because there is suction at the monitor end a leak at that end will cause the gas sample to be diluted.

According to an embodiment of the invention, the monitor device 7 is configured to monitor and indicate if a change in the sample line 8 gas concentrations can be detected with a small and constant delay after every inspiration.

If sampling tube is connected without leaks the flow in the sample line 8 is controlled only by the monitor gas pump. If however there is a leak at the monitor end the flow of the gas in the sample line 8 is also controlled by the pressure in the patient circuit 13. The inspiration phase causes the pressure in the patient circuit to rise.

The matters described above means that the sample line 8 in a leak situation blows more gas to the monitor device 7 every time that there actually is an inspiration phase. This happens without delay. Normally without any leak there is a delay usually present because of the length of the sample line and monitor pump.

The gas in the sample line 8 is the same as in the patient circuit and differs therefore in most situations from the ambient air. If it does not differ it means that there is ambient air in the patient circuit. In this situation the leak does not pose any danger to the patient.

Normally the changes in gas concentrations are not synchronized to happen at several cycles directly after or at the inspiration. Because of the delay of the sample line 8 a change can occasionally happen in the time window but it will wander off. The changes can be arbitrary in amplitude because the sample line 8 can contain inspired or exhaled gases but the changes will be there every time.

A technical effect afforded by embodiments of the invention is that if a change in gas concentrations can be detected at once, i.e. with a small delay, at every inspiration, a leak can with high probability be suspected.

The embodiments described above are by no means intended to restrict the invention but the invention can be modified completely freely within the scope of the claims.

What is claimed is:

1. An anaesthesia machine arrangement comprising:
a gas dispenser; and
a patient circuit connected to the gas dispenser, the patient circuit comprising:
a monitor device having a gas pump and configured to detect a leak by correlating change in measured sampling gas concentration with change in patient circuit pressure,
a control device, and
an interface unit,
wherein the gas dispenser is configured to deliver a desired concentration of fresh gas to the patient circuit, the desired concentration being set by the interface unit,
wherein the monitor device is configured to monitor gas concentration in the patient circuit by drawing gas from the patient circuit through a sample line,
wherein the monitor device is configured to detect the leak when a change in the gas concentration is detected after a determined time delay following each of a plurality of inspirations, and
wherein the control device is configured to control the gas dispenser from the basis of data received from the monitor device to maintain a desired fresh gas concentration.

2. The anaesthesia machine arrangement according to claim 1, wherein the monitor device is configured to monitor the sampling gas concentration changes at a monitor device end of the sample line.

3. The anaesthesia machine arrangement according to claim 1, wherein the monitor device is configured to monitor inspired gas concentrations or/and expired gas concentrations.

4. The anaesthesia machine arrangement according to claim 1, wherein the monitor device is configured to monitor the sampling gas concentration changes at every inspiration.

5. The anaesthesia machine arrangement according to claim 1, wherein the patient circuit further comprises a CO2 absorber.

6. The anaesthesia machine arrangement according to claim 1, wherein the monitor device is configured to provide suction at the monitor end of the sample line.

7. The anaesthesia machine arrangement according to claim 1, wherein the monitor device is configured to provide a continuous supply of suction at the monitor end of the sample line.

8. The anaesthesia machine arrangement according to claim 7, wherein the monitor device is configured to draw inspiration gas and expiration gas through the sample line.

9. The anaesthesia machine arrangement according to claim 1, wherein the monitor device indicates the leak when the monitor device detects the leak.

10. The anaesthesia machine arrangement according to claim 1, wherein the monitor device is configured to detect the leak at the monitor end of the sample line.

11. A method of controlling an anaesthesia machine arrangement, the method comprising:
   monitoring a patient circuit for leaks using a monitor device coupled with the patient circuit by a sample line; and
   indicating a change in a measured sampling gas concentration correlated with a change in a patient circuit pressure,
   wherein the monitor device indicates a leak when a change in the measured sampling gas concentration is detected after a time delay following each of a plurality of inspirations.

12. The method according to claim 11, wherein the monitoring the patient circuit for leaks further comprises:
   measuring the concentration of a gas sample at the monitor device end of the sample line.

13. The method according to claim 11, wherein the monitoring the patient circuit for leaks comprises:
   monitoring one of inspired gas concentration and expired gas concentration.

14. The method according to claim 11, wherein the monitoring the patient circuit for leaks comprises:
   monitoring changes in the concentration of the gas sample at every inspiration.

15. The method according to claim 11, further comprising:
   absorbing $CO_2$ from one of an inspired gas and an expired gas.

16. A method of controlling an anaesthesia machine arrangement, the method comprising:
   setting a desired gas concentration with an interface unit;
   monitoring a patient circuit through a sample line connecting the patient circuit to a monitor device;
   controlling the fresh gas concentration on the basis of data received from the monitor device; and
   monitoring for leaks at a monitor device end of the sample tube by indicating change in measured sampling gas concentration that correlates with change in the patient circuit pressure, wherein the monitor device indicates a leak when a change in the measured sampling gas concentration is detected after a time delay following each of a plurality of inspirations.

* * * * *